United States Patent [19]

Peabody et al.

[11] Patent Number: 5,004,459
[45] Date of Patent: Apr. 2, 1991

[54] CONTINUOUS CYCLIC PERITONEAL DIALYSIS SYSTEM AND METHOD

[76] Inventors: Alan M. Peabody, 102 Meadow Creek Ct., Greer, S.C. 29651; Olin S. Anderson, Jr., 1216 Morven Rd.; Henry H. Morton, 100 Covington St., both of Wadesboro, N.C. 28170

[21] Appl. No.: 200,624

[22] Filed: May 31, 1988

Related U.S. Application Data

[63] Continuation-in-part of Ser. No. 858,645, May 2, 1986, Pat. No. 4,747,822, which is a continuation-in-part of Ser. No. 840,142, Mar. 17, 1986, Pat. No. 4,718,890, which is a continuation-in-part of Ser. No. 629,130, Jul. 9, 1984, Pat. No. 4,586,920.

[51] Int. Cl.$^5$ .............................................. A61M 1/00
[52] U.S. Cl. ........................................ 604/29; 604/31; 604/65
[58] Field of Search .................................... 604/27-31, 604/65-67; 128/DIG. 12, DIG. 13; 210/90, 98, 104, 137, 645, 646

[56] References Cited

U.S. PATENT DOCUMENTS

| | | |
|---|---|---|
| 3,545,438 | 12/1970 | DeVries . |
| 3,620,215 | 11/1971 | Tysk ...................... 604/29 |
| 3,709,222 | 1/1973 | DeVries . |
| 4,190,047 | 2/1980 | Jacobsen et al. .................. 604/29 |
| 4,252,115 | 2/1981 | Schael ...................... 604/29 |
| 4,261,360 | 4/1981 | Perez ...................... 604/31 |
| 4,338,190 | 7/1982 | Kraus ...................... 210/195.2 |
| 4,381,003 | 4/1983 | Buoncristiani ...................... 604/29 |
| 4,412,917 | 11/1983 | Ahjopalo ...................... 604/29 |
| 4,526,568 | 7/1985 | Clemens et al. ...................... 604/28 |
| 4,586,920 | 5/1986 | Peabody ...................... 604/29 |
| 4,618,343 | 10/1986 | Polaschegg ...................... 604/29 |
| 4,718,890 | 1/1988 | Peabody ...................... 604/29 |
| 4,747,822 | 5/1988 | Peabody ...................... 604/29 |
| 4,769,001 | 9/1988 | Prince ...................... 604/28 |

FOREIGN PATENT DOCUMENTS

| | | |
|---|---|---|
| 0088900 | 3/1983 | European Pat. Off. . |
| 2149040 | 10/1972 | Fed. Rep. of Germany . |
| 2371931 | 7/1978 | France . |

Primary Examiner—Stephen C. Pellegrino
Assistant Examiner—Ralph A. Lewis
Attorney, Agent, or Firm—Cort Flint

[57] ABSTRACT

A continuous cycle peritoneal dialysis system which includes a source (14) of dialysis fluid, and an inflow line (34) and outflow line (35) connected to a catheter (26) implanted in the peritoneal cavity (28). A fill pump (B) pumps dialysis fluid from the source to the catheter during a fill cycle. A drain pump C pumps fluid from the catheter to a drain during a drain cycle. A function of a volume of the dialysis fluid in the peritoneal cavity is detected by a manometer (D). A process controller (A) controls the fill and drain pumps in response to signals from a high fluid level detector (50) and a low fluid level detector (52) on a fluid column tube (48) to pump a calibrated fill volume of fluid into the cavity and a calibrated drain volume of fluid out of the cavity continuously in alternating fill and drain cycles in a manner that the fluid flows through the cavity generally with zero dwell time. In the process, an inflow volume of dialysis fluid pumped into the cavity is metered (36b) and an outflow volume of fluid pumped out of the cavity is metered (44b) to determine the amount of fluid removed from the patient by comparing the inflow and outflow volumes.

19 Claims, 2 Drawing Sheets

CONTINUOUS CYCLIC PERITONEAL DIALYSIS SYSTEM AND METHOD

CROSS REFERENCED TO RELATED APPLICATIONS

This application is a continuation-in-part of co-pending application Ser. No. 06/858,645 entitled Continuous Flow Peritoneal Dialysis System and Method filed May 2, 1986, now U.S. Pat. No. 4,747,822, which is a continuation-in-part of application Ser. No. 06/840,142 entitled Continuous Flow Peritoneal Dialysis System and Method, filed Mar. 17, 1986, now U.S. Pat. No. 4,718,890, which is a continuation-in-part of application Ser. No. 06/629,130 entitled Continuous Flow Peritoneal Dialysis System and Method, filed July 9, 1984, now U.S. Pat. No. 4,586,920.

BACKGROUND OF THE INVENTION

The invention relates to a dialysis process for purifying the blood by continuous flow of a dialysate and exchange across the peritoneal membrane.

Heretofore, artificial kidney users have relied basically on two processes for purifying the blood. Hemodialysis involves the circulation of blood through a dialysis machine in which an exchange of toxic metabolites takes place across an artificial membrane outside the patient's body. This process requires the assistance of trained personnel and subjects the patient to dangers of mechanical malfunction due to the fact that blood vessels are involved.

Peritoneal dialysis involves the infusion of a sterile dialysate into the peritoneal cavity and after absorbing waste metabolites, the dialysate is discarded. The process is then repeated until the level of metabolites is reduced to a desired level. This method is commonly referred to as the "Batch" method due to the fact that multiple one or two liter bottles or bags of fresh dialysate solution are utilized which require multiple connections to be made to the catheter inserted in the peritoneal cavity during the dialysis process. The multiple connections made during the course of the dialysis has been thought to be a major cause of the high instance of peritonitis.

Continuous ambulatory peritoneal dialysis offers continuous peritoneal dialysis while still allowing the patient some off time. However, the continuous ambulatory peritoneal dialysis must be done in absence of a machine and multiple bottles or bags of dialysis must be infused daily. Thus, multiple infusions per day requires that multiple connections of bags or bottles to the peritoneal catheter be made. The production of bulk sterile dialysis for the peritoneal process has not been shown to be practical for large scale application particularly for home dialysis.

U.S. Pat. No. 4,311,587 seeks to avoid some of the above problems with peritoneal dialysis by providing a sub-micron filter on line with the fresh dialysate to prevent peritoneal contamination. The system is perambulatory and the bag of dialysate is worn by the patient. The bag may be pressurized by numerous methods and is connected only to the inflow side of the filter. The outflow port of the filter is connected on the other side of the filter so that no peritoneal contaminating source is connected directly to the peritoneal cavity. The system is still basically a batch type system in that multiple bottles or bags of dialysate must be connected to the filter even though direct connection to the peritoneal catheter is not required.

U.S. Pat. No. 4,338,190 discloses a system and process which attempts to avoid the batch process method utilized heretofore in peritoneal dialysis wherein a closed loop peritoneal circuit is provided having a selective membrane across which toxic metabolites are exchanged. A solution is passed on the other side of the selective membrane for maintaining the original concentration of sugar and salt in the peritoneal fluid as the toxic metabolites pass the separator membrane. A concentrate of sugar and salts is mixed at a desired ratio with water making up the dialysis fluid. The conductivity of the fluid may be automatically monitored to adjust the concentration of the fluid during its recirculation. A double peritoneal catheter provides for the inflow and outflow of the peritoneal fluid. However, the peritoneal fluid is constantly recirculated through the peritoneal cavity and the efficiency becomes reduced slightly because of residual toxins which are put back into the peritoneal cavity. The selective membrane is an expensive disposable item which means that the cost of operating the system is high unless the membrane is recleaned. Pumping the peritoneal fluid through the peritoneal cavity is required making it difficult to assure that the patient stays properly distended during the dialysis process. If the peritoneal membrane is not fully distended, it becomes convoluted around the intestines and pockets are formed where the peritoneal fluid can hide. Incomplete circulation then results with decreased efficiency of dialysis. No control is had over the level of peritoneal fluid in the peritoneal circuit. There is no way of replenishing the peritoneal fluid should the circuit run low on fluid or run dry.

U.S. Pat. No. 3,545,438 discloses a batch type peritoneal dialysis method which provides for partially reusing a portion of the dialysis fluid. The spent fluid becomes mixed with fresh dialysate. There is no control or monitoring of the fluid in and out as would allow the dialysate to flow in the peritoneal cavity continuously without dwell time. U.S. Pat. No. 3,707,967, corresponding to German Patent No. 2,149,040, apparently discloses a closed loop dialysis system wherein the dialysis fluid is continuously circulated through the peritoneal membrane. The combination of flow control and monitoring in inflow and outflow lines, and a continuous, cyclic open circuit is not present in the German application. U.S. Pat. No. 3,709,222 discloses a peritoneal dialysis method generally of the batch type. In the U.S. Pat. No. '222, the amount of dialysis fluid entering the peritoneal cavity and the pressure of the peritoneal cavity are controlled by varying the height of a pressure relief chamber. This can be both inaccurate and unreliable, and requires that an attendant be present in order to carry out the process. The cycles involved in the process are rather complicated involving an initial priming cycle which involves the filling of a proportioned chamber, the pressure relief chamber and a return chamber. To begin the process, dialysis fluid s allowed to enter the peritoneal cavity from the pressure relief chamber until the chamber is moved to a lower position which prevents the fluid from flowing. Next, an automatic cycling begins in which the fluid is pumped out of the cavity into the return chamber. Next, an inflow cycle begins in which the fluid is pumped from the return chamber to the proportional chamber which forces fresh dialysis from the proportioning chamber into the pressure relief chamber from where it flows into the patient. Next, there is an equilibrium cycle in which dialysis fluid is drained from the proportioning chamber and fresh dialysis fluid is added. Apparently, during this time, dialysis fluid remains in the cavity. The process then switches back to the outflow cycle in which fluid is pumped from the cavity to the return chamber. French Patent No. 2,371,931 discloses a peritoneal process having a single line used for inflow and outflow. The method includes pumping in a certain amount of dialysate, letting it diffuse for a prescribed dwell time, and removing the dialysate. This is, in essence, an automatic "batch" system.

In the above referenced related co-pending applications, peritoneal dialysis processes are disclosed involving continuous inflows and outflows of fluid using a double catheter in an open loop circuit in which fluid is discarded rather than recirculated. Other aspects of these processes involve using a single catheter open circuit system in which alternating inflow and outflow cycles occur with zero dwell time for the fluid in the cavity. The present invention relates to improvements in the control of these processes and to the control of the osmolality of the fluid in response to the amount of the fluid removed from the patient. The osmolality is continuously adjusted to ensure the basis of the patient.

Accordingly, an important object of the present invention is to provide a continuous cycle peritoneal dialysis system and method which avoid the inherent problems and dangers of a batch type peritoneal dialysis system.

Still another important object of the present invention is to provide a peritoneal dialysis system having a high rate of dialysate exchange providing increased dialysis efficiency.

Still another important object of the present invention is to provide a peritoneal dialysis system and method having a high rate of dialysate exchange and dialysis efficiency in which the osmolality of the fluid is continuously adjusted in response to the amount of fluid removed from the patient.

Still anther important object of the present invention is to provide a continuous-flow single-pass peritoneal dialysis system and method in which the pressure and volume of dialysate in the patient's peritoneal membrane may be monitored and set by the patient in a simple and convenient manner without the need of a medical attendant.

SUMMARY OF THE INVENTION

The above objectives are accomplished according to the present invention by a system and process of peritoneal dialysis in which a continuous flow of sterile dialysis fluid is produced and caused to flow through the peritoneal cavity of the patient in a single-pass open-circuit. The exchange of toxic metabolites occurs across the patient's peritoneal membrane and the residual dialysis solution is drained away after leaving the patient's cavity. Positive displacement fill and drain pumps pump and meter the fluid during the fill and drain cycles. A manometer is connected in the flow line to monitor peritoneal pressure as a function of volume. A high level detector detects a high fluid level in the manometer tube to cut off the fill pump and cycle while starting the drain pump and cycle instantaneously with zero dialysis fluid dwell. A low level detector senses a low fluid level in the manometer tube to instantaneously reverse the drain cycle to a fill cycle. The revolutions of the pumps are counted during the fill and drain cycles to determine the volume of fluid put in and taken out of the cavity. The weight and amount of fluid removed or taken in by the patient is calculated. The glucose concentrate and osmolality of the solution is then varied to provide a desired osmolality and patient weight loss or addition.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
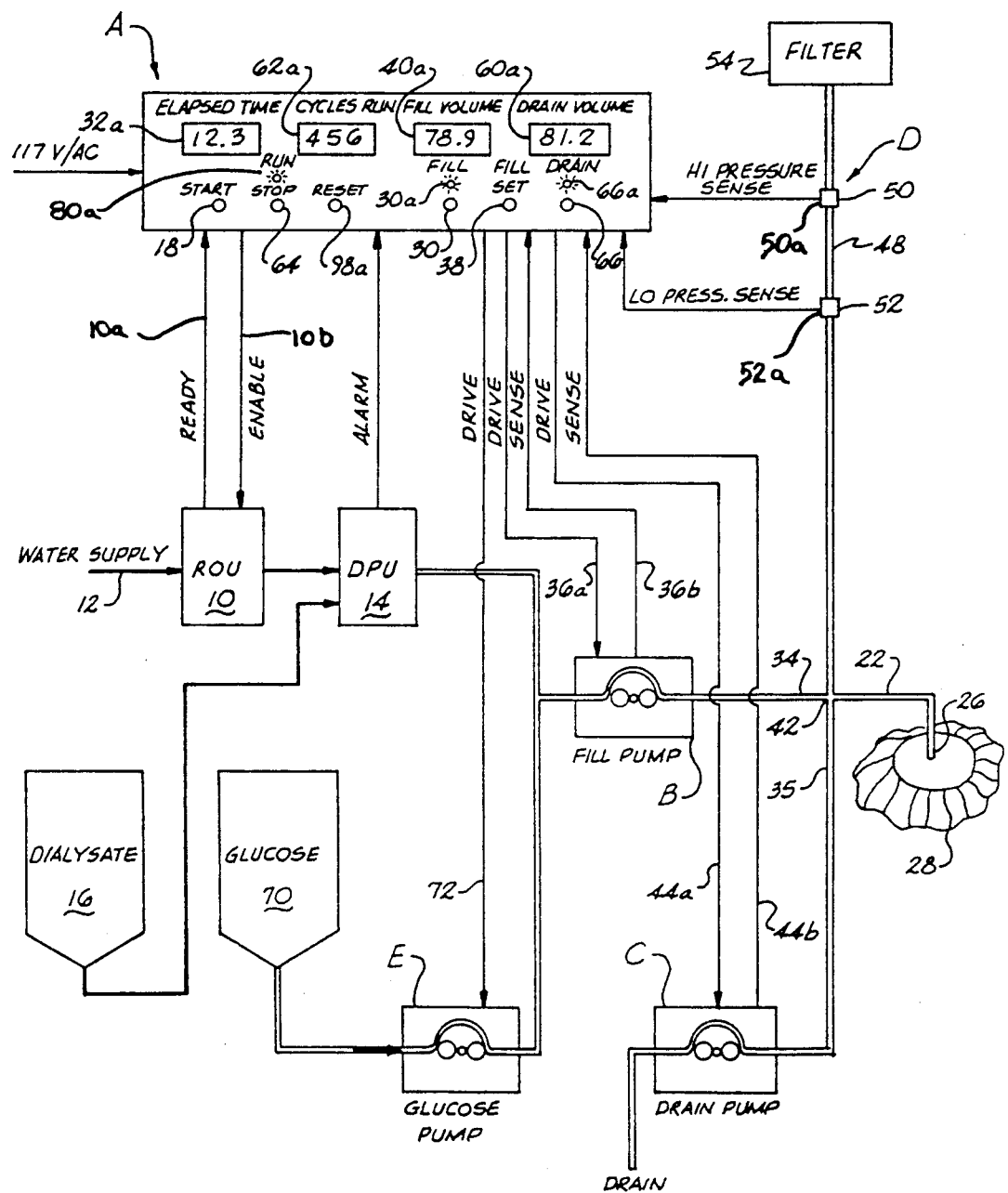
FIG. 1 is a schematic diagram illustrating a continuous flow peritoneal dialysis system and method according to the invention.

Referring now in more detail to the drawings, a continuous inflow/outflow peritoneal dialysis process and system is illustrated in FIG. 1 which includes a water purification and tempering unit 10 connected to a water source 12. Unit 10 may be any suitable unit for sterilizing and tempering the water, such as a conventional reverse osmosis unit. Unit 10 communicates through ready and enable lines 10a, 10b as shown going up to a process controller, designated generally as A. Unit 10 has no intelligence from the process controller other than ready or not ready. A dialysate proportioning unit 14 receives concentrate dialysate from a source 16 and mixes it with sterilized water from unit 10 to provide a concentrated solution of prescribed proportions of dialysate and water. Unit 14 may be a conventional proportioning pump having a geometry that creates a specific ratio of one fluid to another. One fluid drives the pump, the other is pumped by the pump. The fluids come out at a specific fixed ratio. Unit 14 may also include pressure regulation, temperature sensing, conductivity sensing and by-pass and drain valving. This would allow for the system to function in its three modes of operation. The first mode is the sterilize mode which is the static mode of the machine. It is full of some sterilizing solution, perhaps Clorox brand of bleach. The second mode of operation for the machine would be the rinsing and preparation for dialysis mode. The unit is operated in the second mode until conditions are stable and suitable for patient dialysis. The third mode would be the running mode where actual dialysis process is performed. Unit 14 is controlled by dialysis process controller A which is responding to the sensing that is taking place in unit 14 providing data to the process controller. Process controller A may be any suitable process controller of conventional design well within the capacity of one having average skill in the automatic control art.

The system is started by actuation of a start button 18. Once the process controller has gone through the sterilization and is into the run cycle, the dialysis process controller may begin. A run light 20 on controller A will signal the patient that the machine is ready to operate and may include an additional audio, visual, or both signal to the patient. Next, the patient will connect a tube set 22 from the dialysis processing unit to a single flow catheter 26 disposed in the patient's peritoneal cavity 28 in a conventional manner. Once the patient has connected his tube set, he will press a fill button 30 on the dialysis process controller acknowledging that he has done all of the preparation required and is ready to begin the dialysis procedure. At that point a time clock 32 on controller A begins to accumulate time as the cycle is now in process. The time clock displays elapsed time at 32a accumulated throughout the entire cycle whether it is terminated by an alarm or by the patient or by a parameter set as a maximum number of cycles. As long as the machine is operating, then elapsed time 32 is accumulating. The process has now begun and the patient is receiving dialysis fluid from a fill pump B. Pump B, preferably of the peristaltic, roller type, pumps fluid from dialysis proportioning unit 14 through line 34 to tube 22 and cavity 28. Pump B is controlled by processor A. For this purpose, pump B is connected by electrical leads 36a, 36b to controller A for delivering speed and volume signals respectively. The patient continues to receive fluid until a comfort level is reached. The patient will manually set a comfort level by pushing a fill-set button 38 when his initial fill has reached a point which he considers to be a comfortable level and feels his cavity slightly distended. Pressing button 38 will indicate to process controller A that is the fill level or volume he wishes to set and to repeat the dialysis process cycles at that particular volume of fluid. The process controller immediately reverses the cycle from fill to drain without any dwell time for the fluid in cavity 28. All the time the machine was filling under fill volume, the amount of fluid pumped into the patient will be metered by counter 40, and accumulated and displayed at display 40a on controller A. The fill volume 40a is an accumulated total as it pertains to one dialysis process for one patient. This corresponds to elapsed time 32a.

The fill cycle stops and the drain cycle instantaneously begins at the point at which the patient pushes fill-set button 38. When the patient presses the fill set button 38, he also sets a slidable high pressure detector 50 on a manometer means D to correspond to this fill volume. A fluid column tube 48 is connected to junction 42 to receive fluid and is oriented vertically in the fashion of a standpipe. A millipore filter 54 vents tube 48 to atmosphere. Column tube 48 includes high fluid and pressure detector 50 and a low level and pressure detector 52 which provide a manometer means D. Detectors 50, 52 may be standard photocell detectors, or infrared sensors for detecting the presence or absence of fluid at the high and low levels. For this purpose, the detectors may be mounted on slide brackets 50a, 52a, so that the high/low points may be set to particular points. The patient calibrates the high pressure point by sliding detector 50 to the level of fluid seen when the fill set button is pushed. Alternately tube 48 may be slidably mounted. The high and low pressure levels will tend to remain constant for a given patient. Tube 48 is preferably plastic tubing and does not have to be hanging perfectly vertical. This provides a very simple yet sensitive and accurate means of sensing the pressure in the cavity and hence peritoneal volume. As little as 15 centimeters of water, a very slight pressure, may be sensed. After the patient pushes the fill set button and calibrates the high pressure detector 50, operation is automatic. After the fill cycle, controller A, without any dwell, turns on drain pump C, preferably of the peristaltic pump type.

The pump begins to drain fluid from cavity 28. Drain pump C is connected via junction 42 to tube 22. Pump C is controlled by controller A and there are leads 44a, 44b connected to the pump. Lead 44a delivers a speed signal to pump C and lead 44b delivers a sensed volume (rpm) signal to controller A. The drain cycle is a function of the fill-pump stopping and the drain pump starting. Fill pump B and drain pump C are positive displacement type pumps which have the ability to both pump and meter fluids, and constitute a pump means for pumping dialysis fluid through an inflow line during the fill cycle and through an outflow line during the drain cycle. The accumulated fill volume is a function of the pumps pumping in and the drain is a function of pumps pumping out in rpm's. Pump C drains until the pressure in peritoneal cavity 28 no longer supports the column 46 of fluid in column tube 48 attached to junction 42. The fluid height in column tube 48 falls to a prescribed low pressure point detected by lower sensing device 52. Low pressure point 52 may be preset in controller A corresponding to a minimum pressure or it may be calibrated by sliding the detector on the tube. At this point the patient's cavity has drained to a point where the dialysis process has reached diminishing returns. This keeps the cycle time at a minimum. Then the cycle reverses and becomes a fill cycle once again. At this time, the drain volume will be metered by counter 60 and the amount withdrawn from the patient is shown on a controller display 60a as it continues to accumulate. Since this is cycle 1, it will be the exact amount of the initial drain. Cycle run display 62a of cycle counter 62 will increment to 1 showing that the first cycle is completed and another cycle has begun. That cycle will continue until the height of the fluid in the column approaches high pressure sensor 50 and the fluid does not just reach that, it pauses above that and below that. The pumping of pump C is not continuous, it is intermittent pumping action. The pump speed governs the height of the column. As the cavity 28 reaches its fill level, fluid in tube 48 will oscillate rapidly above and below high pressure detector 50 and controller A will slow pump B down. The pump speed has diminished to the point of diminishing returns, the delivery of fluid to the patient is getting ever more slow. When fluid level is generally constant in blocking detector 50, pump B will cut off. Then, the cycle is reversed once again, and a drain cycle is instigated by controller A. The same variable speed operation of pump C occurs during the drain cycle. The reversing cycles continues until the patient terminates it, the maximum time has run out, fill volume has timed out, or until an alarm in the system stops it. At exactly the instant the patient presses stop button 64, the pump is pumping dialysis fluid in with the column height pressure level in every instance. The pump is pumping out with the low pressure maintained at low pressure sensor 52 in every instance. It is the pump speed which corresponds to a maintained column height that determines when the cycle trips.

The setting of the fill volume will now be described in more detail. When fill set button 38 is pressed the pump has reached a certain recorded speed. It is filling up column tube 48. The column height is there and the pump, for example, is at approximately 10 r.p.m. The pump starts out running at full r.p.m. which is about 40 r.p.m. The pump continues at full rate until the column reaches high pressure sensor 50. As soon as the liquid hits this level, it is going above it. It has reached this point through acceleration and is going to continue to go above that point unless the speed of the pump is decreased. As the patient accepts fluid and actually creates more resistance to the fluids, it can enter the patient's body less rapidly. The pump has to slow down to maintain the column height. At the point where the patient becomes uncomfortable, he pushes the fill-set button and the machine immediately reverses. There is a corresponding pump speed which corresponds to fill pressure. The patient may press the fill-set button as frequently as he wishes throughout the entire process. For instance at the start one would probably not be as relaxed and the tissue in the abdomen would not have elasticized and perhaps would have a smaller pool areal. After his body becomes accustomed to the process, he may be able to accept more. Therefore, the patient presses the fill button and the system starts the fill until the patient presses the fill-set button. This would then give the patient a different fill volume level. The pressing of the fill-set button creates a memory of the exact conditions of the unit at the time the button is pressed. Fill is a command to fill that will continue until the fill-set button is pressed or until the system reaches an internally programmed maximum values. These values would include physiology safe values. These values, while not always comfortable to the patient, are physically undamaging. In the event of an emergency, the patient may hit a drain button 66 and then he may release the connector hoses and be released. The value where the machine automatically goes into the drain mode will presumably be something above the comfort level, but not above a safety level. This may be preset in the controller. This is not accessible by the patient.

Means for regulating the osmolality of the dialysis solution delivered to the patient in response to the amount of the fluid removed from the patient is provided. The regulating means continuously adjusts the osmolality of the solution to ensure that a desired amount of fluid is removed, or in some cases, added. The regulating means includes a glucose pump E, preferably of the peristaltic type, connected to the inflow line upstream of fill pump B and the inlet of pump E is connected to a source of glucose 70. Pump E is controlled by controller A in response to the amount of fluid removed from a patient to adjust the glucose concentrate and osmolality of the dialysate coming from source 16 in order to achieve a desired patient weight loss. It is noted that fill pump B and drain pump C are fixed volume roller pumps which quite accurately serve to meter the amounts of fill and drain fluids. By measuring the number of revolutions per minute of the pump and pumping time, the volume of fill and drain fluid may be accurately metered and determined. The same is true of glucose pump E in regard to the amount of glucose pumped and mixed with the dialysis fluid in order to accurately determine the glucose concentrate and osmolality of the solution. For a given patient, the dry weight of that patient can easily be estimated. By weighing the person before dialysis, the amount of weight loss desired during dialysis can be determined. This determines the amount of fluid removed from the patient during dialysis. Based on the length of time the process is to run, the amount and ratio of glucose needed for the desired weight loss can be determined. Controller A calculates the volume of fill and drain fluid from the volumetric r.p.m. signals on leads 36b and 44b from the respective pumps. By comparing these signals, it can be determined how much fluid is being removed from the patient. If the weight, i.e. fluid, is not being adequately removed, a drive signal is sent to glucose pump E from controller A via lead 72 to speed up the pump, increase the glucose supplied to the dialysis fluid, and increase fluid removal. If too much weight is being removed, the glucose pump is slowed down to reduce the amount and ratio of glucose mixed with the fluid. Adjusting the glucose concentrate and osmolality automatically allows for a standard dialysate solution to be supplied at 16. The concentrate can easily be tailored to the patient by varying the glucose amount via pump E. Providing different pre-prepared dialysates for a variety of patients is not necessary as the concentrate may easily be varied in an automatic convenient manner in accordance with the process and system of the invention. The glucose is automatically varied during the dialysis process to achieve a desired weight loss, or addition if the case may be.

Figure 2:
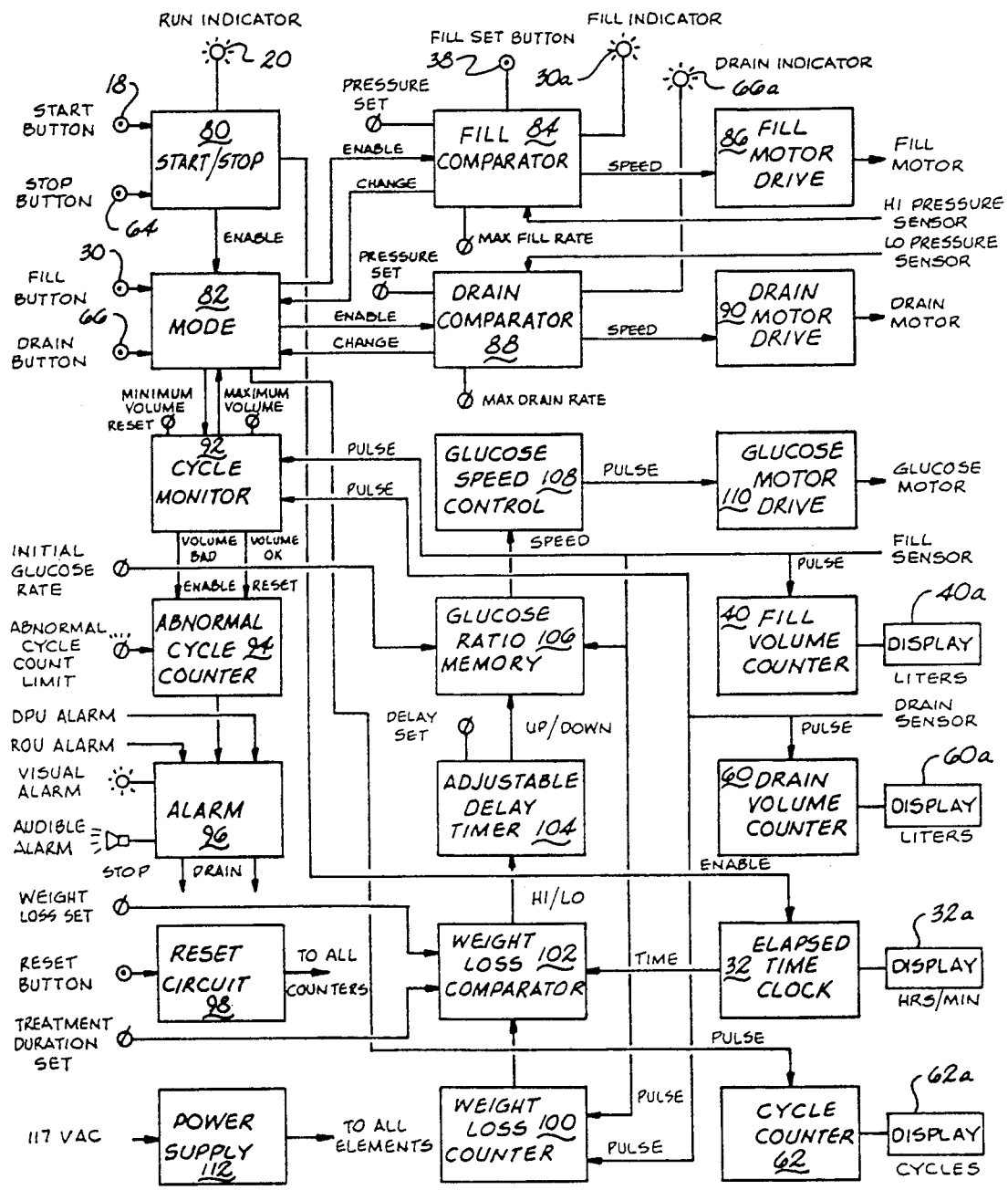
FIG. 2 is a schematic view illustrating a process controller for a continuous cycle peritoneal dialysis system and method according to the present invention.

Referring now in more detail to FIG. 2, a block diagram of one suitable controller is illustrated. There is a start/stop circuit 80 driven by manual push buttons allows starting, stopping, and continuing of the process without losing the control parameters or data accumulated thus far in the event the patient must adjust for position, comfort or temporary interruptions. A run indicator 80a glows when process is proceeding. A mode 82 circuit determines the fill/drain cycle of operations. Fill and drain manual push buttons 30, 66 may be activated at any time to interrupt the automatic control and force a change to the opposite mode. A fill comparator 84 is connected to a motor drive 86 of pump B and monitors the fill mode and limits the fill speed of pump B to the setting on the maximum fill rate and causes the mode circuit to reverse when the peritoneal pressure during any cycle reaches the predetermined maximum value on the pressure set control. A drain comparator 88 is connected to motor drive 90 of drain motor C and monitors the drain mode to limit the drain speed of pump C to the setting on the maximum drain rate and causes the mode circuit to reverse when the peritoneal pressure during any drain cycle reaches the predetermined minimum value on the preset pressure control. Fill set button 38 is used by the patient during the first fill half-cycle of a treatment to establish the maximum fill volume and store in memory. Patient comfort is the criteria for this setting. Fill/drain indicators 30a, 66a show which mode the system is in at the moment. A fill/drain motor drives 86, 90 send power to their respective motors to provide the pumping action desired. Hi/lo pressure sensors 50, 52 monitor the height of the column of dialysate in a tube so placed as to represent the peritoneal pressure. High sensor 50 senses the high pressure level, and low sensor 52 senses the low pressure level. This data is used to control fill/drain rates. Fill/drain motors drive the peristaltic roller mechanisms against the sterile tube-set to pump the dialysate. Fill motor pumps dialysate into the patient's peritoneal cavity. Drain motor pumps the dialysate out of the patient's peritoneal cavity.

A cycle monitor circuit 92 measures the fill and drain volumes of each cycle and compares them to the predetermined values of minimum and maximum volume per half-cycle as set by the minimum volume and maximum volume controls. Should a volume not be in tolerance, a violation signal registers. An abnormal cycle counter 94 counts the violations and if a predetermined number, as set on the abnormal cycle count limit, occur in a row then the process is stopped, drain is initiated, and an alarm circuit 96 is activated. Alarm circuit 96 receives violation signals from either the abnormal cycle counter, the dialysate proportioning unit 14, or the water sterilization unit 10 and triggers an audible alarm and visual alarm until a reset button 98a is pressed. A weight loss counter 100 measures the fill and drain volumes by the pulses from the fill and drain pump sensors 36b, 46b and calculates the instantaneous weight loss volume. A weight loss comparator 102 uses this weight loss value and the elapsed time from elapsed time clock 32 and calculates the weight loss rate which is compared to the predetermined values as set on the weight loss set and treatment duration set controls. If the rate needs to be changed to accomplish the goal, a high or low signal is sent to the adjustable delay timer 104. If the treatment has been in progress for the delay time value as set on the delay set control, then an up-/down signal is sent to the glucose ratio memory circuit 106 to change the ratio from the predetermined value set on the initial glucose rate. This whole evaluation and adjustment process repeats continuously to accomplish the weight loss goal. A glucose speed control 108 accepts this ratio signal and converts it to a pulse rate which drives the stepper-type glucose motor E through the glucose motor drive 110 to effect a highly accurate glucose mix into the dialysate.

Fill and drain volume counters 40 and 60, respectively, measure and display, in liters, the respective accumulated volumes by counting pulses from the fill and drain sensors 36b, 44b which trigger with each revolution of the peristaltic pumps. Elapsed time clock 32 measures and displays the total time the treatment has been in process in hours and minutes. Cycle counter 62 measures and displays the total number of fill and drain cycles. Reset circuit 98 returns all counters and clocks to zero when the reset push button is pressed for 4 seconds. A power supply 112 supplies electrical current for all elements from the standard 117 VAC utility power.

While a preferred embodiment of the invention has been described using specific terms, such description is for illustrative purposes only, and it is to be understood that changes and variations may be made without departing from the spirit or scope of the following claims.

What is claimed is:

1. A continuous cycle peritoneal dialysis process comprising:
    providing a source of a generally continuous and unlimited supply of sterilized dialysis fluid;
    providing an inflow line for connection to a catheter adapted for implantation into the peritoneal cavity of a patient;
    providing an outflow line for connection to said catheter;
    using pump means for pumping sterilized dialysis fluid from said source to said catheter through said inflow line during a fill cycle and for pumping said fluid from said catheter to a drain through said outflow line during a drain cycle;
    monitoring a function of a volume of said sterile dialysis fluid in said peritoneal cavity by determining a high level signal for said dialysis fluid inflow corresponding to a comfortable and efficient cavity distension level of said patient, and setting a low level signal for said dialysis fluid outflow corresponding to a low volume level for dialysis; and controlling said pump means in response to said high level signal to pump a calibrated fill volume of fluid into said cavity and in response to said low level signal to pump a calibrated drain volume of fluid from said cavity continuously in alternating fill and drain cycles;
    delivering said drain volume of fluid pumped out of said cavity to a disposal means so that a single pass of said dialysis fluid occurs through said peritoneal cavity of said patient during said fill and drain cycles;
    calibrating said fill volume and drain volume so that a prescribed amount of dialysis fluid is left in said abdominal cavity between said fill and drain cycles;
    mixing glucose with said dialysis fluid prior to pumping said fluid into said cavity;
    determining the amount of fluid removed from said peritoneal cavity of said patient; and
    adjusting the amount of glucose mixed to vary the glucose concentrate of said fill volume fluid in response to amount of fluid removed from said patient.

2. The process of claim 1 wherein said pump means is provided by a fill pump in said inflow line and a drain pump in said outflow line for pumping said fill and drain volumes of said dialysis fluid from said peritoneal cavity; and including:
    sensing pressure in said inflow line to monitor said function of the volume for stopping said fill pump and starting said drain pump in response to sensing a prescribed high pressure, and stopping said drain pump and starting said fill pump in response to sensing a prescribed low pressure.

3. The process of claim 2 including sensing said pressure by using a manometer means connected in said inflow line capable of sensing slight pressures of 15 or more centimeters of water, and sensing said high and low pressures by detecting respective high and low levels of fluid in said manometer means.

4. The process of claim 2 including generating an alarm signal in response to a prescribe pressure corresponding to an amount of fluid exceeding a prescribed level to avoid over distension of said cavity.

5. The process of claim 1 including measuring an inflow volume of dialysis fluid pumped into said cavity and an outflow volume of fluid pumped out of said cavity to determine the amount of fluid removed from said patient by a comparison of said inflow and outflow volumes.

6. The process of claim 5 including providing a glucose pump connected to a source of glucose and to said inflow line and controlling said pump in response to a comparison of said inflow and outflow volumes to regulate the glucose content and osmolality of said fill volume fluid.

7. The process of claim 1 including controlling said flow of dialysis fluid in said inflow and outflow lines so that dialysis fluid flows in and then out of said peritoneal cavity in a continuous cyclic manner.

8. The process of claim 1 including detecting a fluid level of said dialysis fluid at a high point to terminate said fill cycle and detecting said fluid level at a low point to terminate said drain cycle.

9. The process of claim 8 including calibrating and setting at least said high point of said fluid level manually in response to said patient reaching a desired fill volume level and cavity distension.

10. The process of claim 1 including closing said outflow line when dialysis fluid is flowing into said peritoneal cavity and closing said inflow line while said fluid is flowing out of said cavity.

11. A continuous cyclic peritoneal dialysis system comprising:

a source of a generally continuous supply of sterile dialysis fluid;

an inflow line adapted for connection to said source and to a peritoneal catheter implanted in the peritoneal cavity of a patient;

an outflow line adapted for connection to said peritoneal catheter;

pump means for controlling the flow of dialysis fluid in said inflow and outflow lines to thereby control a fill volume of dialysis fluid pumped into said peritoneal cavity during a fill cycle and a drain volume pumped out of said cavity during a drain cycle so that a prescribed amount of dialysis fluid is left in said abdominal cavity between said fill and drain cycles;

detector means for sensing a function of a volume of dialysis fluid in said peritoneal cavity;

control means controlling said pump means in response to said detector means for starting and stopping said respective fill and drain cycles;

disposal means connected to said outflow line for discharging said drain volume of dialysis fluid and establishing a single-pass open circuit through said peritoneal cavity for dialysis; and regulating means for adjusting the glucose content of said dialysis to vary the osmolality of said dialysis fluid in response to the amount of fluid removed from said patient during the dialysis process.

12. The system of claim 11 wherein said pump means includes a fill pump in said inflow line for pumping fluid into said cavity and a drain pump in said outflow line for pumping said fluid out of said cavity.

13. The system of claim 11 wherein said regulating means includes:

metering means for measuring an inflow volume of fluid pumped into said cavity and for measuring an outflow volume of fluid pumped out of said cavity; and glucose delivery means controlled in response to said metering means for adjusting said glucose content.

14. The system of claim 11 wherein said detector means comprises:

a fluid column tube connected in fluid communication with said inflow and outflow lines having a fluid level indicating pressure;

a high detector for detecting a high level of fluid in said column tube, and a low detector for detecting a low level of fluid in said column tube; and said fill cycle starting in response to said low detector, and said drain cycle starting in response to said high detector.

15. The system of claim 14 wherein at least said high detector and column tube are disposed for relative sliding motion so that said high detector may be set and calibrated manually.

16. The system of claim 11 including:

a glucose pump having an inlet connected to a source of glucose and an outlet connected to said inflow line;

metering means for measuring an inflow volume of fluid pumped into said cavity and for measuring an outflow volume of fluid pumped out of said cavity; and means for adjusting said glucose pump to vary the amount of glucose delivered into said inflow line in response to said inflow and outflow volumes to alter the osmolality of the fluid.

17. The system of claim 16 wherein said pump means includes a fill pump in said inflow line for pumping fluid into said cavity and a drain pump in said outflow line for pumping said fluid out of said cavity; and said metering means includes counters for counting the revolutions per minute of said fill and drain pumps to measure said inflow and outflow volumes respectively.

18. A continuous cyclic peritoneal dialysis process comprising:

providing a dialysis fluid;

commencing a fill cycle by delivering an inflow of said fluid into a peritoneal cavity of said patient;

sensing a function of a peritoneal volume of said fluid in said cavity;

terminating said fill cycle in response to sensing a fill volume;

commencing a drain cycle in response to said fill volume by delivering an outflow of said fluid from said cavity;

terminating said drain cycle in response to sensing a drain volume;

repeating said fill and drain cycles until said process is completed; and regulating the amount of glucose mixed with said fill volume of dialysis fluid in response to a comparison of said volumes of inflow and outflow fluid.

19. The process of claim 18 including:

metering said inflow of fluid to measure an inflow volume, and metering said outflow of fluid to measure an outflow volume; and regulating the amount of glucose mixed with said dialysis fluid to vary the osmolality of the solution in response to a comparison of said metered inflow and outflow volumes continuously during said dialysis process to insure the removal of a proper amount of fluid from said patient.

* * * * *